(12) United States Patent
Huffman et al.

(10) Patent No.: US 6,194,544 B1
(45) Date of Patent: *Feb. 27, 2001

(54) CYCLIC SEMI-RANDOM PEPTIDE LIBRARIES

(75) Inventors: William Francis Huffman, Malvern; Michael Lee Moore, Media, both of PA (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/571,869

(22) PCT Filed: Jul. 9, 1994

(86) PCT No.: PCT/US94/07687

§ 371 Date: Jan. 5, 1996

§ 102(e) Date: Jan. 5, 1996

(87) PCT Pub. No.: WO95/01800

PCT Pub. Date: Jan. 19, 1995

Related U.S. Application Data

(63) Continuation of application No. 08/090,350, filed on Jul. 9, 1993, now abandoned.

(51) Int. Cl.[7] ............................. C07K 7/64; C07K 1/04
(52) U.S. Cl. .................. 530/321; 530/317; 530/334; 530/324; 530/335; 530/329; 530/330; 435/4; 435/DIG. 35; 514/9; 514/2
(58) Field of Search ............... 435/41, DIG. 35; 530/317, 334, 324, 335, 329, 330; 514/9, 2

(56) References Cited

U.S. PATENT DOCUMENTS

| | | | |
|---|---|---|---|
| 5,010,175 | 4/1991 | Rutler et al. | 530/324 |
| 5,114,918 | 5/1992 | Ishikawa et al. | 530/317 |
| 5,270,170 | 12/1993 | Schultz et al. | 435/252.33 |
| 5,288,514 | 2/1994 | Ellman et al. | 530/324 |
| 5,506,337 | 4/1996 | Summerton . | |

FOREIGN PATENT DOCUMENTS

| | | |
|---|---|---|
| WO91/19735 | 12/1991 | (WO) . |
| WO92/00091 | 1/1992 | (WO) . |
| WO92/09300 | 6/1992 | (WO) . |

OTHER PUBLICATIONS

Houghten et al., Nature, vol. 354, pp. 84–86 (1991).
Lam etal., Nature, vol. 354, pp. 82–84 1991.
Lebl et al., Int. J. Peptide Res., 41 (2), pp. 201–203 (1993).
Geysen et al., J. Immunol. Meth., vol. 259, pp. 102 (1987).
Bray et al., Tet. Lett., vol. 31, pp. 5811 (1990).
Bray et al., Tet. Lett., vol. 32, pp. 6163 (1991).
Pinilla et al., Biotechniques, vol. 13, pp. 901 (1992).
Lam et al, Nature, vol. 354, pp. 82–84, (Nov. 1991).*
Lebl et al, Int. J. Peptide Protein Des., vol. 41(2), pp. 201–203, (1993).*
Houghten et al. Nature, vol. 354, pp. 84–86, (Nov. 1991).*
Gordon, et al., J. Med. Chem., 1994, vol. 27, No. 10, pp. 1385–1401.
Koivunen, et al., J. Bio. Chem., 1993. vol. 268, No. 27, pp. 20205–20210.
O'Neill, et al., Chemical Abstracts, vol. 118, No. 11, Abstract No. 94016.
O'Neill, et al., Proteins: Structure, Function & Genetics, 1992, vol. 14, pp. 509–515.
Darlak et al, "Cyclic Peptide Libraries", pp. 981–983, Pept. Chem., Struct. Biol., Proc. Am. Pept. Symp., 13th(1994), meeting date (1993).*

* cited by examiner

Primary Examiner—T. D. Wessendorf
(74) Attorney, Agent, or Firm—Wayne J. Dustman; William T. King; Charles M. Kinzig

(57) ABSTRACT

Cyclic penta- and hexa-peptide libraries containing one or more known amino acids, one or more randomized amino acids and a conformationally constraining element are disclosed. These peptide libraries may be used for screening for new bioactive peptides and for elucidating structural information pertinent to drug design.

9 Claims, No Drawings

CYCLIC SEMI-RANDOM PEPTIDE LIBRARIES

This application is a 35 U.S.C. §371 national stage application of PCT/US94/07687, filed Jul. 9, 1994; which is a continuation of U.S. Ser. No. 08/090,350, filed Jul. 9, 1993, which is now abandoned.

FIELD OF THE INVENTION

This invention relates to random and semi-random peptide libraries, methods of preparing such libraries and methods for screening such libraries to select peptides which have desirable binding characteristics to target molecules or biological systems of interest.

BACKGROUND

Random peptide libraries are generally envisioned as a collection of peptide sequences in which all amino acids have been incorporated randomly into all positions of the peptide. The library will therefore contain $l^n$ different peptides where peptides of l residues have been constructed from n different amino acids. Each peptide in the mixture will have a unique sequence and all possible sequences for an l-residue peptide will be represented. Such libraries have been generated and used in various ways to screen for peptide sequences which bind effectively to target molecules and to identify such sequences.

One methodology to generate a random library involves expressing peptides of random composition on a virus such as the filamentous phage. Peptides are encoded by preparing randomized oligonucleotides $(NNC/T)_n$, where N is a random base (and T represents the stop codon). The nucleotides are inserted into the gene coding for a protein expressed on the phage surface, typically either the pVIII major coat protein or the pIII tail protein.

There are several chemical methods of preparing random libraries. One method for preparing a totally random library has been disclosed by Lam et al., *Nature*, 354, 82, (1991) and PCT/US91/04666 (WO 92/00091). The method involves synthesis of linear peptides on a solid support such as polystyrene or polyacrylamide resin. The resins are separated into 18 pools for incorporation of a single amino acid for each pool using standard solid phase synthesis methodology. After coupling, the pools of resin are recombined and redistributed into 18 pools again for coupling of a second amino acid. Each individual bead will contain a unique peptide sequence and, given a sufficient number of beads, all possible peptide sequences will be represented in the peptide library. The essence of the method is that the resin-linked peptide can be probed with some soluble receptor or antibody and beads which react with the probe can be isolated and individually sequenced using typical Edman sequencing chemistry. In addition, PCT/US91/08694 (WO 92/09300) discloses methodologies to provide selectively cleavable linkers between peptide and resin such that a certain amount of peptide can be liberated from the resin and assayed in soluble form while some of the peptide still remains attached to the resin, where it can be sequenced. See also, Lebl et al., *Int. J. Pept. Prot. Res.*, 41, 201 (1993).

Another methodology disclosed by Geysen et al. *J. Immunol. Meth.*, 259, 102, (1987) involves the synthesis of peptides on derivatized polystyrene pins which are arranged on a block in such a way that they correspond to the arrangement of wells in a 96-well microtiter plate. Individual chemical reactions can be performed on each pin in a single well and thus individual peptides can be prepared on each pin. The pins are typically probed using an Elisa type of double antibody assay which is also carried out in the microtiter wells. In the mimotope approach, random dipeptides are synthesized on the pins and probed with the target antibody. The best dipeptide is selected and a series of tripeptides based on the original dipeptide plus one more residue are prepared and probed. The best tripeptide is used as the basis of a tetrapeptide and so on until an optimized sequence up to an octapeptide has been determined. The strategy allows for incorporation of non-natural amino acids or D-amino acids into the peptides. In order to circumvent the necessity of a soluble "receptor," a cleavable linker has been described which will release the peptide from the pins involving a C-terminal ϵ-Lys-Pro sequence, see Bray et al., *Tet. Lett.*, 31, 5811(1990) or via ammonolysis, see Bray et al., *Tet. Lett.*, 32, 6163 (1991).

Another approach to de novo determination of antibody or receptor binding sequences but involving soluble peptide pools is that of Houghten et al., *Nature*, 354, 84 (1991). Using simultaneous solid phase synthesis, hexapeptides are prepared in which unique amino acids are coupled at two defined positions in the sequence and an equimolar mixture of amino acids is used for the couplings for the remaining four positions. The resulting peptides can be represented by the sequence $O_1$-$O_2$-X-X-X-X, [SEQ ID NO.: 1] where $O_1$ and $O_2$ are defined amino acids and X represents the randomized amino acids. For peptides constructed of 18 amino acids, there are $18^2$ or 324 different peptide mixtures or pools, each mixture consisting of $18^4$ or 104,976 individual peptides with a single defined residue for $O_1$ and $O_2$. Each of the 324 pools is assayed for activity and the best selections for $O_1$ and $O_2$ are used as the basis to vary the next residue, i.e., constructing peptides of the sequence $A_1$-$A_2$-$O_3$-X-X-X [SEQ ID NO.: 2], where $A_1$ and $A_2$ are the optimized residues, $O_3$ is the defined amino acid which will be varied, and X is the random pool of amino acids. This process is repeated iteratively until an optimized sequence is obtained. The process can be streamlined considerably by preparing hexapeptides containing only one amino acid to be varied, i.e., the 18 peptides $O_1$-X-X-X-X-X [SEQ ID NO.: 3], the 18 peptides X-$O_2$-X-X-X-X [SEQ ID NO.: 4], etc. for a total of 6×18 or 108 peptide pools. Each pool is assayed and the best residues for each position are determined. See, Pinilla et al., *Biotechniques*, 13, 901 (1992) and PCT patent application WO 92/09300 (Iterex Pharmaceuticals). These techniques relate to linear peptides.

Linear peptides historically have represented relatively poor objects for drugs and for pharmaceutical design. Linear peptides are able to adopt a multitude of conformations and hence are able to bind in various ways to a single target molecule and may bind to various target molecules in various conformations. Molecules which are rigid or able to adopt a limited number of conformations bind more selectively to target molecules. In addition, linear peptides have presented difficulties in drug development and there is no rational strategy for conversion of a linear peptide into a non-peptide drug.

The use of resin-bound cyclic peptides and free cyclic peptides in combinatorial libraries are disclosed in PCT/US91/04666 (WO 92/00091) and Darlak et al., Proceedings of the 13th American Peptide Symposium, 2–193, P902 (1993). These cyclic peptides do not contain a conformationally constraining element and where cyclization is possible, these peptides generally may adopt a large number of conformations and suffer many of the same shortcomings as linear peptides.

The present invention improves the quality of the peptide and the lead for rational drug design derived from random libraries by introducing defined conformational constraints. Peptides and leads derived from the templates of this invention not only optimize side chain position but also overall conformation, which is a significant advantage in any peptide drug and any effort to rationally design non-peptide ligands. The present invention also eliminates the need for stepwise peptide sequencing, and the requirement for a soluble target molecule which are shortcomings of some of the prior random libraries.

SUMMARY OF THE INVENTION

An object of this invention is to provide useful peptide libraries for screening for bioactive molecules.

A feature of this invention is the preparation of cyclic peptide libraries. Another feature of this invention is the preparation of cyclic peptide libraries which have constrained conformations. Yet another feature of this invention is the screening of such cyclic peptide libraries to select cyclic peptides which have a binding affinity for target molecules or bioactivity in biological systems.

DETAILED DESCRIPTION

This invention is a composition comprising a set of cyclic homodetic penta- and hexa-peptide libraries each library comprising a variable mixture of amino acids at one or more positions, and a defined amino acid in at least one position. In particular, this invention comprises a set of peptide libraries wherein the peptide backbone of the libraries has a well-defined peptide backbone conformation.

In a general form this invention is a set of cyclic peptide libraries of the formula (I):

[$X^1$-$X^2$-$X^3$-$X^4$-$X^5$-$X^6$] [SEQ ID NO.: 5]    (I)

wherein $X^1$, $X^2$, $X^3$, $X^4$, $X^5$ and $X^6$ are each independently, a variable mixture of amino acids, provided that at least one residue is defined and one residue is optionally absent In another embodiment this invention is a set of peptide libraries in which at least one amino acid is a constant amino acid. In a preferred embodiment one to three amino acids are constant and comprise a conformationally constrictive element.

A "library" of peptides indicates a collection of peptides wherein at least one defined amino acid is present. Typically the amino acid in other positions of the peptide will be "randomized" or "constant" if they are not defined. Each library is characterized by its defined amino acid residues, its constant residues and its variable amino acid residues. A "set" of libraries indicates a group of n libraries wherein n indicates the number of defined amino acid residues in a given position. A set of libraries wherein two positions contain a defined amino acid will consist of $n^2$ libraries.

A "variable" position or amino acid residue may have more than one amino acid in the specified position of the peptide.

A "defined" amino acid residue is a residue whose identity and position in the peptide is known. Typically, in a set of libraries, each library differs from the other in the identity of its defined amino acid(s) (e.g., the defined amino acid(s) will be constant throughout a single library, yet differ between libraries within the set). A "constant" amino acid or sequence is one whose identity and position are invariant throughout the peptides of the library, and across a set of libraries. As used herein, both constant and variable amino acid residues are indicated by an "O". Superscripts serve merely to distinguish one defined or constant residue from another.

A "randomized" position or amino acid residue is a position in the peptide wherein all amino acids which comprise the amino acid set are represented in the library. As used herein, a randomized amino acid residue is indicated by an "X". Superscripts serve merely to distinguish one randomized residue from another.

An equimolar mixture of randomized amino acids is a mixture in which each amino acid in the randomized amino acid set is present in the same molar amount.

An "optimized" amino acid residue is that amino acid of the amino acid set which has the optimal activity (e.g., biological response, binding or inhibition of biological response or binding) when a library having a defined amino acid is screened for a given target activity. Preferably, only a single amino acid will confer optimal activity. An optimized residue is characterized by its identity and position in the peptide sequence, and may also be a function of the positional sequence in which various defined amino acids are introduced into the library and tested for activity. As used herein, an optimized amino acid residue is indicated by an "A". Superscripts serve merely to distinguish one optimized amino acid residue from another.

The "amino acid set" comprises all amino acids which are to be varied within the peptide at a particular position. Typically the amino acid set will comprise 2–50 different amino acid residues. The amino acid set may be varied in the number of amino acid residues and types of residues for each position in the peptide, or the same set may be used for all positions in the peptide. For instance, the set may consist of all naturally occurring L-amino acids for all positions throughout a hexapeptide, or it may consist of all naturally occurring L-amino acids for positions 1, 3 and 5 and both L- and D-amino acids for positions 2, 4 and 6.

Amino acids include compounds with have an amino terminus and carboxy terminus, preferably in a 1,2-, 1,3-, or 1,4-substitution pattern on a carbon backbone. α-Amino acids are most preferred, and include the 20 natural amino acids (which are L-amino acids except for glycine), which are found in proteins, the corresponding D-amino acids, the biosynthetically available amino acids which are not found in proteins (e.g., 4-hydroxy-proline, 5-hydroxy-lysine, citrulline, ornithine, canavanine, djenkolic acid, β-cyanoalanine), and synthetically derived α-amino acids, such as amino-isobutyric acid, norleucine, norvaline, $C^α$ alkylated and $N^α$ alkylated amino acids, Dtc, Tpr, homocysteine and homoserine. β-Alanine and γ-amino butyric acid are examples of 1,3-and 1,4-amino acids, and many others are well known to the art. Statine-like isosteres (a dipeptide comprising two amino acids wherein the CONH linkage is replaced by a CHOH), hydroxyethylene isosteres (a dipeptide comprising two amino acids wherein the CONH linkage is replaced by a CHOHCH$_2$), reduced amide isosteres (a dipeptide comprising two amino acids wherein the CONH linkage is replaced by a CH$_2$NH linkage) and thioamide isosteres (a dipeptide comprising two amino acids wherein the CONH linkage is replaced by a CSNH linkage) are also useful residues for this invention.

As used herein "peptide" indicates a sequence of amino acids linked by peptide bonds. The peptides of this invention comprise a sequence of amino acids of 4 to 6 amino acid residues, each residue being characterized by having an amino and a carboxy terminus.

As used herein the designation of square brackets surrounding an amino acid sequence indicates a cyclic peptide wherein an amino terminus is joined to a carboxy terminus, e.g., in the case of α-amino acids the α-amino group of the first residue is joined to the carboxy group of the last residue. A cyclic peptide formed in such a manner is termed a homodetic peptide.

It will be appreciated that in a cyclic peptide, due to the symmetry of the molecule, the positions of all defined and variable amino acid residues are relative. For instance, when one amino acid is defined (indicated by O) and all others are randomized, the collection represented by $[O^1\text{-}X^2\text{-}X^3\text{-}X^4\text{-}X^5\text{-}X^6]$ [SEQ ID NO.: 6] is identical to $[X^1\text{-}O^2\text{-}X^3\text{-}X^4\text{-}X^5\text{-}X^6]$, $[X^1\text{-}X^2\text{-}O^3\text{-}X^4\text{-}X^5\text{-}X^6]$, $[X^1\text{-}X^2\text{-}X^3\text{-}O^4\text{-}X^5\text{-}X^6]$, $[X^1\text{-}X^2\text{-}X^3\text{-}X^4\text{-}O^5\text{-}X^6]$ and $[X^1\text{-}X^2\text{-}X^3\text{-}X^4\text{-}X^5\text{-}O^6]$. Similarly, $[O^1\text{-}X^2\text{-}O^3\text{-}X^4\text{-}X^5\text{-}X^6]$ [SEQ ID NO.: 6] is identical to $[O^1\text{-}X^2\text{-}X^3\text{-}X^4\text{-}O^5\text{-}X^6]$ and so on. Although it may be useful during the synthesis of the library to prepare a defined amino acid in a specific position in the linear peptide to facilitate cyclization, the use herein of letters in the description of the cyclic peptides is not intended to denote the absolute position of the residue in any synthetic intermediate.

The conformation of a peptide backbone is determined by the three dihedral angles φ ($C\text{-}N\text{-}C_\alpha\text{-}C$), ψ ($N\text{-}C_\alpha\text{-}C\text{-}N$) and ω ($C_\alpha\text{-}C\text{-}N\text{-}C_\alpha$), which not only specify the position of the peptide backbone atoms, but also the angle of projection of the amino acid side chains (Ca-Cb vector) from the peptide backbone. A peptide with a "well defined backbone conformation" will either be rigid, existing in only a single conformer characterized by specific values of φ, ψ and ω for each residue, or will exist as an equilibrium mixture of a relatively few discrete conformers, the torsional angles of all residues for each conformer being well described. Thus, a cyclic peptide with a well defined backbone conformation indicates one in which the atoms and bonds which constitute the ring are energetically able to assume only a limited number of positions in space relative to one another at or around room temperature, and these positions may be well defined by conventional techniques of molecular modeling and crystallography.

Certain abbreviations are used herein to describe this invention and the manner of making and using it. For instance, t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the carbobenzyloxy radical, BrZ refers to the o-bromobenzyloxycarbonyl radical, ClZ refers to the o-chlorobenzyloxycarbonyl radical, Bn refers to the benzyl radical, Mts refers to 4-methoxy-2,3,6-trimethylbenzenesulfonyl, Pmc refers to pentamethylchroman-6-sulfonyl, Ts refers to toluenesulfonyl, DMAP refers to dimethylaminopyridine, DIEA refers to diisopropyl-ethyl amine, Aib refers to 2-amino-isobutyric acid, Dtc refers to 5,5-dimethylthiazolidine-4-carboxylic acid, Tpr refers to thiazolidine-4-carboxylic acid, Trt refers to trityl, HOBT refers to 1-hydroxybenzotriazole, THF refers to tetrahydrofuran, DMF refers to dimethyl formamide, BOP refers to benzotriazol-1-yloxy-tris(dimethylamino) phosphonium hexafluorophosphate, DCC refers to dicyclohexylcarbodiimide, DPPA refers to diphenylphosphoryl azide, EDC refers to N-ethyl-N'-(dimethylaminopropyl)-carbodiimide, HBTU refers to (1-hydroxybenztriazolyltetramethyl-uronium hexafluorophosphate)/N-methylmorpholine, PPA refers to 1-propanephosphonic acid cyclic anhydride, HF refers to hydrofluoric acid, LAWESSON's Reagent is 2,4-bis(4-methoxyphenyl)-1,3-dithia-2,4-diphosphetane-2,4-disulfide and THF is tetrahydrofuran and TFA refers to trifluoroacetic acid. A SASRIN® resin is a 3-methoxy-4-hydroxymethyl-phenoxymethylated 1% divinylbenzene cross linked polystyrene, and is used an orthogonal protection scheme with Fmoc-protected amino acids. A PAM resin is a 4-(hydroxymethyl)phenyl-acetamidomethyl 1% divinylbenzene crosslinked polystyrene, and is used in an orthogonal protection scheme with Boc-protected amino acids. HMPB resin refers to an aminobenzyl or benzhydrylamine divinylbenzene crosslinked polystyrene resin to which a 4-hydroxymethyl-3-methoxyphenoxybutanoic acid (HMPB) group is attached as a cleavable linker between the resin and the first amino acid, and is used with Fmoc-protected amino acids. Rink resin is a (2,4-dimethoxyphenyl)-hydroxymethyl)phenoxy-methyl 1% divinylbenzene cross linked polystyrene resin.

The amino acids used in this invention are those which are available commercially or are available by routine synthetic methods. Certain residues may require special methods for incorporation into the peptide, and both sequential and convergent synthetic approaches to the linear peptide are useful in this invention. For instance, a thioamide isostere is introduced into a peptide by synthesizing a dipeptide, treating the dipeptide with LAWESSON's reagent to convert the amide to a thioamide, such as described by Klausen et al., *Chemica Scripta*, 20, 14 (1982), and introducing the dipeptide into the nascent peptide sequence. A reduced amide isostere may be introduced into tne peptide by reacting a terminal free amine with the amino aldehyde (prepared from the corresponding amino acid) and reducing the imine, as described for instance by Sasaki et al., PEPTIDES, vol. 8, 119 (1987) or Hochart et al., *J. Med. Chem.*, 31, 1820 (1988). Hydroxyethylene isosteres are well known and are prepared as described for instance by Evans et al., *J. Org. Chem.*, 50, 4615 (1985) and Kempf, *J. Org. Chem.*, 51, 3921(1986).

The general methodology for preparing the cyclic peptides of this invention involves solid phase peptide synthesis using an orthogonal protection scheme which allows for chain elongation, cleavage of the side-chain protected peptide from the solid support, cyclization of the protected peptide mixture followed by deprotection of the side chains. It is desirable that the various random peptide sequences be present in the libraries in substantially equal amount. Several methods for preparing the random sequences of the cyclic peptides of this invention are available.

One method of preparing a set of libraries of cyclic homodetic penta- or hexa-peptides containing a randomized mixture of amino acids at one or more positions, which comprises:

a) dividing the resin into n different aliquots, wherein n is the number of amino acid residues in the defined amino acid set;

b) coupling exhaustively to each aliquot in any order:
  (1) a single variable amino acid of the set (e.g., coupling a different amino acid of the randomized set to each aliquot);
  (2) a constant amino acid (e.g., coupling the same amino acid to all aliquots); or
  (3) a defined amino acid;

c) recombining and mixing the aliquots containing the variable amino acids (e.g., and carrying the aliquots containing the defined amino acids on separately);

d) removing the protective group from a reactive functional group on the amino acid;

e) repeating steps (a) to (d) to couple the next residue if the next residue is a variable or defined amino acid, or repeating steps (b) to (d) to couple the next residue if the next residue is a constant amino acid, until five or six residues have been added, f) cleaving the peptide from the resin, g) cyclizing the peptide, and h) removing any protective groups.

The method disclosed in WO 92/00091 (Bioligand) describes a similar method of division and recombination of the library to incorporate amino acid residues randomly into a library for linear peptides. In such a scheme, a constant amino acid residue or conformationally constraining motif may be incorporated by coupling the entire library exhaustively, at any residue, with the constant amino acid(s) without dividing the library into aliquots.

Another method of incorporating random amino acids into a peptide is described in U.S. Pat. No. 5,010,175. According to that method, a mixture of amino acids is incorporated by coupling a mixture in which the individual amino acids are present in varying proportions depending upon their relative rates of reaction in the coupling, e.g., the amount of amino acid is inversely proportional to its rate of coupling.

Another method for preparing a set of libraries of cyclic homodetic penta- or hexa-peptides containing a randomized mixture of amino acids at one or more positions, which comprises:

a) coupling to a resin in any order:
   (1) an equimolar mixture of a randomized amino acid set in an amount equal to the number of reactive functional groups on the resin (e.g., one reactive amino acid is present for each reactive site on the resin);
   (2) a constant amino acid; or
   (3) separating the resin into n separate aliquots and coupling a defined amino acid to each aliquot (and carrying on each aliquot separately), wherein n is the number of amino acid residues in the defined amino acid set;

b) removing the protective group from a reactive functional group on the amino acid;

c) repeating step (a) and coupling the next residue to the reactive functional group of the previous amino acid until five or six residues have been added, d) cleaving the peptide from the resin, e) cyclizing the peptide, and f) removing any protective groups.

Typically the coupling between the resin and the first amino acid will form an ester bond, which will yield a carboxylic acid group on the peptide when it is cleaved from the resin. SASRIN®, HMPB, Rink, PAM and hydroxymethyl resins are exemplary.

The coupling reactions are performed by methods to create amide or ester bonds and are performed by methods familiar in the art as described herein. Typical coupling reagents are carbodiimides, activated anhydrides and esters and acyl halides. Reagents such as EDC, DCC, DPPA, HPTU, PPA, BOP reagent, HOBT, N-hydroxysuccinimide and oxalyl chloride are typical.

The reactive functional groups of the sidechains of each amino acid or peptide are suitably protected as known in the peptide art. For example, the Boc, Cbz or Fmoc group may be used for protection of an amino group, especially an α-amino group. An alkyl (e.g., t-Bu, Me), cHex or benzyl ester may be used for the protection of the side chain carboxyl of Asp or Glu. A benzyl, or suitably substituted benzyl, trityl or t-Bu group is used to protect the mercapto group of cysteine, or other thiol containing residues; or the hydroxyl of Tyr, Ser or Thr. Cys and other sulfur-containing amino acids may also be protected by the acetamido group or by formnation of a disulfide with a thioalkyl (e.g., ethyl mercaptan) or thioaryl group. The benzyl/benzyloxymethyl, or a suitably substituted benzyl/benzyloxymethyl, Boc or formyl group may be used for protection of the imidazolyl group of His; and the Pmc, nitro or a suitably substituted benzene-sulfonyl group (e.g., Ts, Mts) for protection of the guanidino nitrogen of Arg. The phthalamido, Boc, Fmoc, carbobenzyloxy or benzyl group, or suitably substituted benzyl or benzyloxy group, may be used for protecting the ε-amino group of lysine. Suitable substitution of the carbobenzyloxy or benzyl protecting groups is substitution with one to five chloro, bromo, nitro, methoxy or methyl groups, usually ortho and/or para, and is used to modify the reactivity of the protective group. These protective groups are removed by such methods as catalytic hydrogenation, sodium in liquid ammonia, hydrazine, base, TFA or HF treatment, as known in the art. The choice of sidechain protecting groups is chosen so that they will not be removed under conditions which are used to deprotect the reactive functional group used in the coupling reaction (e.g., generally the α-amino group) to form the linear peptide chain. The protective group of the reactive functional group is removed prior to coupling each successive amino acid.

The peptides are cleaved from the resin support by methods known in the art, the precise method being dependent upon the characteristics of the resin. Rink resin, HMPB and SASRIN® resins are generally cleaved by dilute acid, such as 1% TFA in dichloromethane. It will be understood by those skilled in the art that the removal of certain protecting groups may occur simultaneously with cleavage of the peptide from the resin.

The cyclization reaction is merely another coupling reaction in which the terminal amino group of the linear peptide is coupled to the terminal carboxy group of the peptide. DPPA is particularly useful reagent for conducting the coupling reaction. It may be useful to do the coupling under solution conditions of high dilution.

A typical scheme for preparing involves using super acid-labile resin such as a Rink resin, SASRIN® or HMPB resin as the support, Fmoc as the α-amino protecting group and t-butyl based protecting groups for the side chains and Pmc (pentamethylchroman-6-sulfonyl) for the guanidine side chain of Arg. Other schemes of orthogonal protection known to those skilled in the art are obviously applicable as well. Generally, one will calculate the number of possible unique random peptide sequences based upon the length of the peptide chain and the number of amino acids in the amino acid set for each position in the peptide, and will use sufficient resin so that there is at least a ten-fold molecular excess of reactive sites on the resin to the number of possible randomized peptide sequences.

When the C-terminal amino acid is randomized, it is convenient to begin the synthesis using a mixture of individual aminoacyl peptide resins with an equimolar distribution of the amino acids used. An equimolar mixture of the same protected amino acids is also prepared. An aliquot of the protected amino acid mixture corresponding to exactly one equivalent of total amino acid is allowed to couple to the resin mixture. A typical standard, rapid coupling method such as HBTU coupling is used and the coupling reaction is allowed to proceed overnight. The use of exactly one equivalent of total amino acid and the long coupling time serves partially to correct for the different rates of coupling of the individual amino acids in the mixture and to help ensure that an equimolar mixture of amino acids is obtained at each position. At this point, a Kaiser test may be performed to assess the completeness of coupling and recoupling with one equivalent of the equimolar mixture can be performed as necessary.

Addition of the equimolar mixture of protected amino acids can proceed in a stepwise fashion up to the point where the defined amino acid will be added. At that point the resin is partitioned into a number of equivalent aliquots corresponding to the number of amino acids used for the mixture. Each resin aliquot is treated individually from this point on. Each aliquot is coupled to a single amino acid using standard solid phase methodology. If further randomized residues need to be added to the sequence, they are added as an equimolar mixture as before, again taking care that there is exactly one equivalent of total amino acid per equivalent of peptidyl resin.

Upon completion of peptide sequence, the protected peptide mixture is cleaved from the resin by treatment with dilute (1–2%) trifluoroacetic acid in methylene chloride and the filtrate from this reaction is neutralized with an organic base like pyridine in methanol. The side-chain protected peptide mixture is precipitated by the addition of ethyl ether and is collected by centrifugation or filtration.

The side-chain protected peptide mixture is cyclized in DMF using 1.1 equivalents of diphenylphosphoryl azide and 2.2 equivalents of tertiary base such as diisopropylethylamine. The concentration of peptide is approximately 5 mM and reaction is allowed to proceed for several h at room temperature and then overnight at 4° C. The solvent is removed by evaporation and the side chains of the cyclic peptide mixture are deblocked by treatment with a mixture of trifluoroacetic acid, anisole, water (and optionally ethanedithiol) at room temperature for 2 h. The deprotected peptide is precipitated by the addition of ethyl ether and is collected by centrifugation or filtration. The fully deprotected cyclic peptide mixture is then dissolved in 10% aqueous acetic acid and passed over a gel filtration column to remove residual organic impurities. The entire peptide peak is collected and lyophilized, giving one pool of the cyclic peptide library.

Linear peptides possess, for all practical purposes, an incalculable number of potential conformations. Accordingly, they are maximally pliable in being able to adopt a very great number of conformations in which to bind to a target molecule. Conversely, they may not give much information regarding the conformation in which they bind to the target molecule. For instance, it is not possible to know if the peptide is binding in a high or low energy conformation. Relative to the corresponding linear peptides, cyclized peptides which by their conformation position functional groups in a favorable location for binding often are more potent and selective. Thus, the functional groups on the sidechains of the amino acids are able to assume a reduced number of positions in space relative to one another. Since cyclized peptides are not able to achieve what may constitute a low energy conformation for the linear peptide, they may spend more time in a favorable conformation. In addition, since they cannot achieve certain conformations, they may not bind to as many extraneous molecules as the corresponding linear peptide which may result in enhanced selectivity.

Cyclization of a linear peptide to yield a homodetic peptide imposes a constraint on the number of conformations available to the cyclic peptide. The allowed conformations and their energies can be evaluated using methods of molecular modeling, and the skilled chemist can make certain assumptions regarding the favorable positions of functional groups in peptides which bind to the target molecule. This, in turn, aids in the rational design of other molecules, for instance nonpeptides, which have favorable binding properties. The peptides of this invention are preferably of 5 or 6 residues, because cyclic peptides of larger size possess less conformational rigidity, and are generally are not amenable to analysis. Even peptide of 5 or 6 residues are able to adopt a larger number of conformations rendering analysis difficult and the spatial orientation of their constituents less well determined.

The number of allowed conformations can be further reduced by incorporating conformationally constraining element into the cyclic peptides. Conformationally constraining elements are an amino acid residue, or a combination of amino acid residues, which by their inherent structure create energy barriers to rotation about certain bonds in the backbone of the cyclized peptide. Hence, the number of available conformations for the cyclic peptide is reduced further so that the peptide has a well defined backbone conformation. Examples of conformationally constraining elements are a Pro or an Aib residue, a reduced dipeptide isostere, or a thioamide isostere, which induce a γ-turn in a pentapeptide; Pro-D-Pro, which induces a β-turn in a cyclic hexapeptide; and D-Pro-Gly-Pro, which induces an extended backbone conformation in a cyclic hexapeptide. Such elements are disclosed, for instance, by Peishoff et al., *J. Med. Chem.*, 35, 3962 (1992). These elements have their effect by restricting rotation about certain bonds by steric hindrance due to their possessing a bulky group (e.g., Aib, $C_\alpha$-methyl amino acids, $N_\alpha$-methyl amino acids), or by incorporating elements of the carbon backbone in a ring structure (e.g., Pro) or by forming a hydrogen bond with ajoining residues (e.g., thioamide isostere, dipeptide isostere). Other conformationally constrictive elements may be designed or selected from the art using these principles.

Since the efficiency and completeness of cyclization in a peptide mixture cannot be accurately monitored, and indeed may not be energetically favored, certain peptides may not be substantially cyclized during the cyclization reaction. Typically, long reaction times are employed and the site of cyclization is chosen so that the amino acid least likely to racemize occupies the carboxy terminal position of the linear peptide (e.g., to minimize racemization). Accordingly, in another aspect, this invention is an improved method for cyclizing a linear peptide which comprises incorporating a conform nationally constraining element in the peptide in a position to induce efficient cyclization. Preferably the conformationally constraining element will be incorporated into the middle portion of the peptide, such that the terminal amino and carboxy groups are brought into spatial proximity by the conformationally constraining element.

Thus, the linear peptides of this invention are preferably designed for optimal cyclization. For instance, as described herein, when one incorporates a proline residue in order to induce a further conformational constraint upon the peptide (e.g., a γ-turn) placing it in the third position of the linear peptide facilitates rapid and substantially complete cyclization. In such case, the rate of cyclization seems to be largely independent of the nature of the other four amino acids, and cyclization is substantially complete in approximately one hour at room temperature using DPPA. This may be contrasted to the case in which the proline is incorporated in the same peptide, but cyclization is effected with the proline in a terminal (e.g., first or fifth) position of the peptide. Cyclization in the latter case takes approximately 3 days to run to substantial completion.

It is within the skill of one in the art to devise motifs for conformational constraints, for instance by molecular modeling, routine synthesis, and, if necessary, crystallization and crystal structure analysis. One may determine the proper placement for a conformationally constraining motif by studying the effect on a few simple peptides which are included within the library and incorporate the constraint. For instance, Pro and Aib are preferably located in the 3 position of a pentapeptide; Pro-D-Pro are preferably located in the 3 and 4 positions, and Pro-Gly-Pro are typically located in the 2, 3 and 4 positions of the linear hexapeptide.

Using a convergent approach, one may find an optimized binding peptide for the target molecule. According to the convergent approach, one screens a semi-random set of libraries wherein at least one amino acid residue is defined. If n is the number of amino acids in the defined amino acid set, this will result in the screening of n libraries. Based upon the results of the screen, one identifies the library (or the few libraries) which has the optimal activity. The library having optimal activity is characterized by the identity and position of its defined amino acid. A second set of libraries is constructed in which the optimal defined amino acid is identified in the first screen is constant throughout the libraries and a second residue is defined. This second set of libraries is screened, the optimal defined residue is identified, and a new set of libraries is constructed wherein both of the previously identified optimal defined amino acids are constant throughout the library. The process is repeated iteratively until all residues of the peptide are optimized. It is of course within the purview of one skilled in the art to create libraries wherein more than one defined amino acid is present, and this would require the screening of $n^d$ libraries, wherein n is as previously defined and d is the number of defined amino acid residues. When a conformational constraining motif is present in the peptide, the identity and position of the residues constituting the motif will be constant throughout all libraries.

Variations of this convergent procedure may occur by the method in which one converges upon the optimal peptide. In this manner more than one optimal peptide may be identified. For instance, one may optimize the peptide by iteratively optimizing each residue in sequence from the carboxy terminus of the first defined amino acid. Alternately, one may optimize each residue in sequence from the amino terminus of the first identified residue. Such convergent schemes would result in the preparation of sets of libraries of the form:

$[O^1-X^2-X^3-X^4-X^5-X^6]$ [SEQ ID NO.: 6]
$[O^1-O^2-X^3-X^4-X^5-X^6]$ [SEQ ID NO.: 8],
$[O^1-O^2-O^3-X^4-X^5-X^6]$ [SEQ ID NO.: 9],
$[O^1-O^2-O^3-O^4-X^5-X^6]$ [SEQ ID NO.: 10],
$[O^1-O^2-O^3-X^4-O^5-X^6]$ [SEQ ID NO.: 11],
$[O^1-O^2-O^3-O^4-O^5-X^6]$ [SEQ ID NO.: 12],
wherein
$X^1$, $X^2$, $X^3$, $X^4$, and $X^6$ are a randomized mixture of amino acids,
$X^5$ is a mixture of amino acids or is absent,
one of $O^1$-$O^4$ are a defined amino acid and the remaining residues are a constant amino acid, and
$O^5$ is a defined amino acid, a constant amino acid or is absent.

In another variation, one may optimize every other residue from the first defined amino acid. Thus, sets of libraries may be of the form:

$[O^1-X^2-O^3-X^4-X^5-X^6]$ [SEQ ID NO.: 7],
$[O^1-X^2-X^3-O^4-X^5-X^6]$ [SEQ ID NO.: 13],
$[O^1-X^2-O^3-O^4-X^5-X^6]$ [SEQ ID NO.: 14],
$[O^1-X^2-X^3-O^4-O^5-X^6]$ [SEQ ID NO.: 15],
$[O^1-X^2-O^3-X^4-O^5-X^6]$ [SEQ ID NO.: 16],
wherein
$X^1$, $X^2$, $X^3$, $X^4$, and $X^6$ are a randomized mixture of amino acids,
$X^5$ is a mixture of amino acids or is absent,
one of $O^1$-$O^5$ are a defined amino acid and the remaining residues are a constant amino acid.

Geysen et al., *Biorg. Med. Chem. Lett.*, 3, 397 (1993) describe an approach for optimizing linear peptides.

This invention also constitutes a method for using the libraries of this invention which comprises identifying a peptide having a desired activity with respect to a substrate. According to this method a library is contacted with the target molecule and the interaction between the peptides of the library and the target molecule or a biological system is assessed. Common methods of quantifying the interaction are by binding assays and bioactivity assays. The peptides of this invention are well suited to such assays since, unlike immobilized peptide libraries, they may interact with both soluble and immobilized target molecules.

Procedurally, the process for selecting a binding ligand for a substrate comprises:

a) screening a collection of libraries of cyclic homodetic penta- or hexa-peptides against said substrate wherein each library has a first defined amino acid in at least one position and a randomized mixture of amino acids at one or more positions, b) determining the library having maximal activity, c) determining the identity of said first amino acid in the library having maximal activity, d) creating a second collection of libraries of cyclic homodetic penta- or hexa-peptides wherein said first amino acid is that identified as having maximal activity, and a second amino acid is defined for each library, e) determining the library having maximal activity, f) determining the identity of said second amino acid, g) repeating steps (d) to (f) until the maximal activity sequence has been identified for all positions.

The "binding ligand" will be one or more of the peptides in the library or set of libraries. The "substrate" will generally be a target molecule or a biological system which is capable of demonstrating some interaction, such as binding or a biological response. Typical substrate target molecules are a protein, carbohydrate, nucleic acid, lipid, glycoprotein, glycolipid, virus or bacteria or drug, or, more particularly, a receptor, antibody, enzyme, growth factor, hormone, or an agonist or antagonist of a growth factor or hormone. The substrate may also be a biological system, such as a cell, tissue, organ or organism, or homogenate of a cell, tissue, organ or organism. For example, the substrate may be a virus, bacterium or fungus (any of which may be expressing natural or cloned target molecules), a tissue homogenate, such as from brain tissue, kidney tissue or vascular tissue, or a cultured mammalian cell line or preparation, such as a blood, bone, skin or nerve cell line (again, any of which may be expressing natural or cloned target molecules).

The determination of the maximal activity may be either by determining the library with maximal binding, or maximum or minimum inhibition, stimulation, or other biological response. Binding assays are a well known and convenient method for detection of a binding ligand. For instance, one may measure the ability of a library to inhibit or displace the binding of a radioactive ligand from a target molecule, cell or tissue homogenate. Direct enzyme-linked immunosorbent assays (ELISA), indirect ELISA and competitive ELISA are a convenient method, well known in the art, for the measurement of antibody binding to target molecules, and/or the identification of the presence of a marker molecule (e.g., mediator release).

Bioactivity assays are generally cell based or tissue-based assays in which the degree of biological response is measured. For example, the degree of cytotoxicity, ion flux, change in polarization, amount of mediator released, stimulation, growth, contraction, or other physiological change resulting from contact between the peptide library and the target molecule or cell, is measured. Alternatively, by controlling the concentration of the peptide library, an effective dose to cause a given percent of the biological response may be measured (e.g., concentration to cause a 50% response [$EC_{50}$] or concentration to cause a 50% inhibition of response [$IC_{50}$]). Bioactivity assays may be coupled to other assays, such as binding assays, so that the quantification is indirect. Such methods are well known in the art.

The practice of the method of selecting a binding ligand may lead to the identification of a therapeutic agent for the treatment, prevention or amelioration of disease, or the performance or enhancement of some biological function. For instance, a therapeutic agent identified by the method may be an enzyme inhibitor, receptor agonist, receptor antagonist, antimicrobial agent or vaccine. Moreover, the identification of a binding ligand may also lead to the identification of derivatives and analogs of the binding ligand which may have enhanced biological activity.

The Examples which follow are intended to illustrate how to make and use the libraries and methods of this invention and are in no way considered to be a limitation.

EXAMPLE 1

Identification of an inhibitor of the binding of endothelin to its natural receptor using a pentapeptide library constrained by cyclization and a constant Pro residue. Considering the Pro to be residue 1, the set comprises the natural L-amino acids (excepting Cys and Pro) for residue 3, the D-isomers of the natural amino acids (excepting Cys and Pro) for residue 2, 4 and 5. (it will be appreciated, however, that Pro occupies the third position in the linear peptide to promote efficient cyclization.)

General Procedure for Construction of the Peptide Library

An equimolar mixture of 0.2 mmol equivalents of commercial Fmoc-Ala-SASRIN® resin, Fmoc-Arg(Pmc)-SASRIN® resin, Fmoc-Asn(Trt)-SASRIN® resin, Fmoc-Asp(t-Bu)-SASRIN® resin, Fmoc-Gln(Trt)-SASRIN® resin, Fmoc-Glu(t-Bu)-SASRIN® resin, Fmoc-Gly-SASRIN® resin, Fmoc-His(Trt)-SASRIN® resin, Fmoc-Ile-SASRIN® resin, Fmoc-Leu-SASRIN® resin, Fmoc-Lys(Boc)-SASRIN® resin, Fmoc-Met-SASRIN® resin, Fmoc-Phe-SASRIN® resin, Fmoc-Ser(t-Bu)-SASRIN® resin, Fmoc-Thr(t-Bu)-SASRIN® resin, Fmoc-Trp-SASRIN® resin, Fmoc-Tyr(t-Bu)-SASRIN® resin and Fmoc-Val-SASRIN® resin was prepared and thoroughly mixed, giving 3.6 mmol Fmoc-X-SASRIN® resin. An aliquot of resin was hydrolyzed in HCl/propionic acid 1:1, 130° C., 4 h. and shown by amino acid analysis to contain all 18 of the amino acids in roughly equimolar amounts.

A stock solution of Fmoc-D-amino acids was prepared by dissolving 0.8 mmol each Fmoc-D-Ala, Fmoc-D-Arg(PMC), Fmoc-D-Asn, Fmoc-D-Asp(t-Bu), Fmoc-D-Gln, Fmoc-D-Glu(t-Bu), Fmoc-Gly, Fmoc-D-His(Trt), Fmoc-D-Ile, Fmoc-D-Leu, Fmoc-D-Lys(Boc), Fmoc-D-Met, Fmoc-D-Phe, Fmoc-D-Ser(t-Bu), Fmoc-D-Thr(t-Bu), Fmoc-D-Trp, Fmoc-D-Tyr(t-Bu) and Fmoc-D-Val in a total volume of 40 mL DMF.

The Fmoc-X-SASRIN® resin was deblocked with 20% piperidine in DMF for 20 min, washed with DMF and then coupled to a 10-mL aliquot of the stock solution, equivalent to 3.6 mmol of total amino acid, using 3.6 mmol HBTU and 7.2 mmol DIEA in DMF overnight. Ninhydrin test indicated that complete coupling had not occurred, so the coupling was repeated with the same amounts of reagents for two h. Ninhydrin test was negative, indicating complete coupling to yield Fmoc-D-X-X-SASRIN® resin.

An aliquot of Fmoc-D-X-X-SASRIN® resin was hydrolyzed in HCl/propionic acid 1:1, 130° C., 4 h. and subjected to amino acid analysis, which showed that the ratio of amino acids was identical to that of the Fmoc-X-SASRIN® resin, indicating that approximately equimolar amino acid coupling had been obtained.

The Fmoc-D-X-X-SASRIN® resin was deblocked and washed as before and then coupled to Fmoc-Pro (10,8 mmol, 3 equiv.) using HBUT (10.8 mmol, 3 equiv.) and DIEA (21.6 mmol, 6 equiv.) overnight. Ninhydrin test was negative, indicating complete coupling to give Fmoc-Pro-D-X-X-SASRIN® resin.

The Fmoc-Pro-D-X-X-SASRIN® resin was deblocked and washed as before and then coupled as before to an aliquot of the Fmoc-D-X stock solution containing 3.6 mmol total amino acid using 3.6 mmol HBTU and 7.2 mmol DIEA in DMF overnight. Ninhydrin test indicated that complete coupling had not occurred, so the coupling was repeated with the same amount of reagents for 4 h. Ninhydrin test was negative, indicating complete coupling to yield Fmoc-D-X-Pro-D-X-X-SASRIN® resin. The resin was washed and dried overnight in vacuo to yield 7.4 g. This was partitioned into 18 equal aliquots of 0.41 g each for completion of the library.

Library 1

Preparation of Cyclo [D-$O^4$-D-$X^5$-$Pro^1$-D-$X^2$-$X^3$]

A defined amino acid at residue 4.

a) cyclo[D-Ala-D-X-Pro-D-X-X] (1)

A 0.41 g (equivalent to 0.2 mmol) aliquot of the tetrapeptide resin Fmoc-D-X-Pro-D-X-X-SASRIN® resin was deprotected with 20% piperidine/DMF, 20 min, washed with DMF and coupled to 0.6 mmol Fmoc-D-Ala using 0.6 mmol HBTU and 1.2 mmol DIEA for 3 h. Ninhydrin test was positive so the coupling was repeated with the same amount of reagents overnight. Ninhydrin test was negative, and the peptidyl resin was again deblocked with 20% piperidine/DMF, washed and dried overnight.

The protected peptide was cleaved from the resin with 5 mL 1% TFA/$CH_2Cl_2$ for 2 min filtered under low argon pressure directly into a centrifuge tube containing 10% pyridine/MeOH. This process was repeated 4 times, each time using a fresh centrifuge tube containing 10% pyridine/MeOH. The pyridine/MeOH solutions were reduced to about half their volume and the peptide precipitated by the addition of ether. The peptide was collected by centifugation, the ether decanted and the peptide resuspended in ether and centrifuged again. This was repeated twice and the peptide then air-dried overnight. The dried precipitates were combined to yield 130 mg.

The protected linear peptide was dissolved in 10 mL DMF followed by 30 µL (0.22 mmol, 1.1 equiv.) triethylamine. The solution was cooled to 0 ° C. and 43 L diphenylphosphoryl azide (0.20 mmol, 1 equiv.) was added. The solution was allowed to warm to room temperature and was stirred overnight. The solvent was then removed under vacuum and the residual glass dried overnight.

The residue was treated with a mixture of 10 mL TFA, 0.5 mL thioanisole, 0.5 mL water and 0.5 mL ethanedithiol for 2 h. The mixture was transferred to 2 centrifuge tubes and the peptide precipitated by addition of ice-cold ether. The peptide was collected by centrifugation and washed 2 times with ether. The precipitate was then collected by filtration, air-dried, dissolved in glacial acetic acid and lyophilized, yielding 29.9 mg cyclic peptide.

The peptide was dissolved in 10% HOAc, applied to a 1.6×60 cm SEPHADEX G-15, a polysaccharide resin for gel filtration, column and eluted with 10% HOAc. All the UV-positive ($A_{254}$) material was collected, pooled and lyophilized to yield 28.0 mg of the title peptide pool.

b) cyclo[D-Arg-D-X-Pro-D-X-X] (2)

The linear protected peptide D-Arg(Pmc)-D-X-Pro-D-X-X was prepared and cleaved from the resin as in (1), yielding 226 mg. The peptide was cyclized and the side chains deprotected as in (1), yielding 64.8 mg after lyophilization. The cyclic peptide was passed over a 1.6×60 cm SEPHADEX G-15 column and eluted with 10% HOAc. All the UV-positive ($A_{254}$) material was collected, pooled and lyophilized to yield the title peptide pool.

c) cyclo[D-Asn-D-X-Pro-D-X-X] (3)

The linear protected peptide D-Asn-D-X-Pro-D-X-X was prepared and cleaved from the resin as in (1), yielding 173 mg. The peptide was cyclized and the side chains deprotected as in (1), yielding 46.6 mg after lyophilization. The cyclic peptide was passed over a 1.6×60 cm SEPHADEX G-15 column and eluted with 10% HOAc. All the UV-positive ($A_{254}$) material was collected, pooled and lyophilized to yield the title peptide pool.

d) cyclo[D-Asp-D-X-Pro-D-X-X] (4)

The linear protected peptide D-Asp(t-Bu)-D-X-Pro-D-X-X was prepared and cleaved from the resin as in (1), yielding 140 mg. The peptide was cyclized and the side chains deprotected as in (1), yielding 35.9 mg after lyophilization. The cyclic peptide was passed over a 1.6×60 cm SEPHADEX G-15 column and eluted with 10% HOAc. All the UV-positive ($A_{254}$) material was collected, pooled and lyophilized to yield the title peptide pool.

e) cyclo[D-Gln-D-X-Pro-D-X-X] (5)

The linear protected peptide D-Gln-D-X-Pro-D-X-X was prepared and cleaved from the resin as in (1), yielding 203 mg. The peptide was cyclized and the side chains deprotected as in (1), yielding 71.2 mg after lyophilization. The cyclic peptide was passed over a 1.6×60 cm SEPHADEX G-15 column and eluted with 10% HOAc. All the UV-positive ($A_{254}$) material was collected, pooled and lyophilized to yield the title peptide pool.

f) cyclo[D-Glu-D-X-Pro-D-X-X] (6)

The linear protected peptide D-Glu(t-Bu)-D-X-Pro-D-X-X was prepared and cleaved from the resin as in (1), yielding 151 mg. The peptide was cyclized and the side chains deprotected as in (1), yielding 38.8 mg after lyophilization. The cyclic peptide was passed over a 1.6×60 cm SEPHADEX G-15 column and eluted with 10% HOAc. All the UV-positive ($A_{254}$) material was collected, pooled and lyophilized to yield the title peptide pool.

g) cyclo[Gly-D-X-Pro-D-X-X] (7)

The linear protected peptide Gly-D-X-Pro-D-X-X was prepared and cleaved from the resin as in (1), yielding 120 mg. The peptide was cyclized and the side chains deprotected as in (1). The cyclic peptide was passed over a 1.6×60 cm SEPHADEX G-15 column and eluted with 10% HOAc. All the UV-positive ($A_{254}$) material was collected, pooled and lyophilized to yield the title peptide pool.

h) cyclo[D-His-D-X-Pro-D-X-X] (8)

The linear protected peptide D-His(Trt)-D-X-Pro-D-X-X was prepared and cleaved from the resin as in (1), yielding 113 mg. The peptide was cyclized and the side chains deprotected as in (1). The cyclic peptide was passed over a 1.6×60 cm SEPHADEX G-15 column and eluted with 10% HOAc. All the UV-positive ($A_{254}$) material was collected, pooled and lyophilized to yield the title peptide pool.

i) cyclo[D-Ile-D-X-Pro-D-X-X] (9)

The linear protected peptide D-Ile-D-X-Pro-D-X-X was prepared and cleaved from the resin as in (1), yielding 144 mg. The peptide was cyclized and the side chains deprotected as in (1). The cyclic peptide was passed over a 1.6×60 cm SEPHADEX G-15 column and eluted with 10% HOAc. All the UV-positive ($A_{254}$) material was collected, pooled and lyophilized to yield the title peptide pool.

j) cyclo[D-Leu-D-X-Pro-D-X-X] (10)

The linear protected peptide D-Leu-D-X-Pro-D-X-X was prepared and cleaved from the resin as in (1), yielding 289 mg. The peptide was cyclized and the side chains deprotected as in (1). The cyclic peptide was passed over a 1.6×60 cm SEPHADEX G-15 column and eluted with 10% HOAc. All the UV-positive ($A_{254}$) material was collected, pooled and lyophilized to yield the title peptide pool.

k) cyclo[D-Lys-D-X-Pro-D-X-X] (11)

The linear protected peptide D-Lys(Boc)-D-X-Pro-D-X-X was prepared and cleaved from the resin as in (1), yielding 213 mg. The peptide was cyclized and the side chains deprotected as in (1). The cyclic peptide was passed over a 1.6×60 cm SEPHADEX G-15 column and eluted with 10% HOAc. All the UV-positive ($A_{254}$) material was collected, pooled and lyophilized to yield the title peptide pool.

l) cyclo[D-Met-D-X-Pro-D-X-X] (12)

The linear protected peptide D-Met-D-X-Pro-D-X-X was prepared and cleaved from the resin as in (1), yielding 246 mg. The peptide was cyclized and the side chains deprotected as in (1). The cyclic peptide was passed over a 1.6×60 cm SEPHADEX G-15 column and eluted with 10% HOAc. All the UV-positive ($A_{254}$) material was collected, pooled and lyophilized to yield the title peptide pool.

Using the procedure of 1(a), except substituting the appropriate amino acid for D-Ala, the following libraries are prepared.

m) cyclo[D-Phe-D-X-Pro-D-X-X] (13)
o) cyclo[D-Ser-D-X-Pro-D-X-X] (14)
p) cyclo[D-Thr-D-X-Pro-D-X-X] (15)
q) cyclo[D-Tyr-D-X-Pro-D-X-X] (16)
r) cyclo[D-Val-D-X-Pro-D-X-X] (17)
s) cyclo[D-Trp-D-X-Pro-D-X-X] (18)

Libraries 2–5

Using the same amino acid set for the respective positions and following the procedures of Example 1(a)–1(s), except substituting the appropriate defined amino acids in the appropriate position, the following libraries are prepared:

cyclo[D-X-D-O-Pro-D-X-X] (20)
cyclo[D-X-D-X-Pro-D-O-X] (21)
cyclo[D-X-D-X-Pro-D-X-O] (22)

Libraries 6–8

Conducting an endothelin binding assay using Libraries 1–18, the library having the greatest inhibition of endothelin binding is identified. The known amino acid at position 4 corresponding to that library having the greatest inhibition of endothelin binding ($A^4$), is used as the basis for constructing Library 6 of the formula cyclo[D-$A^4$-D-$O^5$-$Pro^1$-D-$X^2$-$X^3$], wherein positions 1 and 4 are constant amino acid residues, following the procedures of Example 1(a)–1(s), except substituting the appropriate defined amino acid in position 5.

Conducting an endothelin binding assay using Library 6, the library having the greatest inhibition of endothelin binding is identified. The known amino acid at position 5 corresponding to that library having the greatest inhibition of endothelin binding ($A^5$), is used as the basis for constructing Library 7, cyclo[D-$A^4$-D-$A^5$-Pro$^1$-D-$O^2$-$X^3$], wherein positions 1, 4 and 5 are constant amino acid residues, is generated following the procedures of Example 1(a)–1(s), except substituting the appropriate defined amino acid in position 2.

Conducting an endothelin binding assay using Library 7, the library having the greatest inhibition of endothelin binding is identified. The known amino acid at position 2 corresponding to that library having the greatest inhibition of endothelin binding ($A^2$), is used as the basis for constructing Library 8, cyclo[D-$A^4$-D-$A^5$-Pro$^1$-D-$A^2$-$O^3$], wherein positions 1, 2, 4 and 5 are constant amino acid residues, is generated following the procedures of Example 1(a)–1(s), except substituting the appropriate defined amino acid in position 3.

Conducting an endothelin binding assay using Library 8, the library having the greatest inhibition of endothelin binding is identified. The known amino acid at position 3 corresponding to that library having the greatest inhibition of endothelin binding ($A^3$) is identified, and this completes the optimized pentapeptide sequence cyclo[D-$A^4$-D-$A^5$-Pro$^1$-D-$A^2$-$A^3$], for an inhibitor of endothelin binding using the aforementioned amino acid set.

Using a similar approach, except optimizing the amino acid residues in a different or variable order, such as by starting with Libraries 2–5, the optimal binding sequence may be confirmed or other optimized peptide binding sequences may be identified for inhibition of endothelin binding. Additional optimized sequences may be obtained by varying the amino acid set used for the various positions.

Binding Assay for Inhibition of Endothelin (ET) Binding
A) Membrane Preparation

Rat cerebellum or kidney cortex were rapidly dissected and frozen immediately in liquid nitrogen or used fresh. The tissues, 1–2 g for cerebellum or 3–5 g for kidney cortex, were homogenized in 15 mL of buffer containing 20 mM Tris HCl and 5 mM EDTA, pH 7.5 at 4° C. using a motor-driven homogenizer. The homogenates were filtered through cheesecloth and centrifuged at 20,000×g for 10 min at 4° C. The supernatant was removed and centrifuged at 40,000×g for 30 min at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 mg of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 mL volume for ~6 gm of mesenteric artery bed. The homogenate was strained through cheesecloth and centrifuged at 2,000×g for 10 min. at 4° C. The supernatant was removed and centrifuged at 40,000×g for 30 min. at 4° C. The resulting pellet was resuspended as explained above for cerebellum and kidney cortex. Approximately 10 mg of membrane protein was used for each tube in binding experiments.

B) [$^{125}$I]ET-1 Binding Protocol

[$^{125}$I]ET-1 binding to membranes from rat cerebellum (2–5 mg protein/assay tube) or kidney cortex (3–8 mg protein/assay tube) were measured after 60 min incubation at 30° C. in 50 mM Tris HCl, 10 mM $MgCl_2$, 0.05% BSA, pH 7.5 buffer in a total volume of 100 mL. Membrane protein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and nonspecific binding were measured in the absence and presence of 100 nM unlabeled ET-1. After the incubation, the reactions were stopped with 3.0 mL cold buffer containing 50 mM Tris and 10 mM $MgCl_2$, pH 7.5. Membrane bound radioactivity was separated from free ligand by filtering through WHATMAN GF/C filter paper and washing the filters 5 times with 3 mL of cold buffer using a Brandel cell harvester. Filter papers were counted in a gamma counter with an efficiency of 75%.

This invention is not limited in scope to the foregoing embodiments described, and various modifications of the procedures described will be apparent to those skilled in the art. Such modifications are included within this invention which is limited only by the spirit of the claims which follow. The disclosures of the various publications which are cited herein are intended to describe the state of the art and are incorporated herein in their entirety as if fully set forth.

What is claimed is:

1. A combinatorial library comprising a set of cyclic homodetic penta- or hexa-peptide libraries each library comprising an equimolar amount of a random mixture of amino acids at one or more positions, and a defined amino acid and a constant amino acid in at least one position and wherein the peptide backbone of the library has a well-defined peptide backbone conformation, provided that the cyclic hexapeptide or pentapeptide contain a conformationally constraining element selected form Pro-D-Pro or D-pro-Gly-pro.

2. The combinatorial library of claim 1 wherein the cyclic homodetic peptide library has the formula:

[$O^1$-$X^2$-$X^3$-$X^4$-$X^5$-$X^6$] [SEQ ID NO.: 6],
[$O^1$-$O^2$-$X^3$-$X^4$-$X^5$-$X^6$] [SEQ ID NO.: 8],
[$O^1$-$O^2$-$O^3$-$X^4$-$X^5$-$X^6$] [SEQ ID NO.: 9],
[$O^1$-$O^2$-$O^3$-$O^4$-$X^5$-$X^6$] [SEQ ID NO.: 10],
[$O^1$-$O^2$-$O^3$-$X^4$-$O^5$-$X^6$] [SEQ ID NO.: 11], or
[$O^1$-$O^2$-$O^3$-$O^4$-$O^5$-$X^6$] [SEQ ID NO.: 12], wherein $X^2$, $X^3$, $X^4$, and $X^6$ are a randomized mixture of amino acids, of equimolar amount, $X^5$ is a random mixture of amino acids or is absent, one of $O^1$-$O^4$ are a defined amino acid and the remaining residues are a constant amino acid, and $O^5$ is a defined amino acid, a constant amino acid or is absent.

3. The combinatorial library of claim 1 wherein the cyclic homodetic peptide library has the formula:

[$O^1$-$X^2$-$O^3$-$X^4$-$X^5$-$X^6$] [SEQ ID NO.: 7],
[$O^1$-$X^2$-$X^3$-$O^4$-$X^5$-$X^6$] [SEQ ID NO.: 13],
[$O^1$-$X^2$-$O^3$-$O^4$-$X^5$-$X^6$] [SEQ ID NO.: 14],
[$O^1$-$X^2$-$X^3$-$O^4$-$O^5$-$X^6$] [SEQ ID NO.: 15], or
[$O^1$-$X^2$-$O^3$-$X^4$-$O^5$-$X^6$] [SEQ ID NO.: 16], wherein $X^2$, $X^3$, $X^4$, and $X^6$ are a randomized mixture of amino acids, of equimolar amount, $X^5$ is a random mixture of amino acids or is absent, one of $O^1$-$O^5$ are a defined amino acid and the remaining residues are a constant amino acid.

4. The combinatorial library of claim 2 wherein $O^1$-$O_2$ or $O^1$-$O^2$-$O^3$ comprise a conformationally constrictive element of Pro-D-Pro or D-Pro-Gly-Pro.

5. The combinatorial library of claim 2 wherein $O^1$ is Pro, or $O^1$-$O^2$ is D-Pro-Pro, or $O^1$-$O^2$-$O^3$ is D-Pro-Gly-Pro.

6. The combinatorial library of claim 5 comprising the sequence [Pro-$X^2$-$X^3$-$X^4$-$X^6$] in which $X^2$,$X^4$ and $X^6$ are amino acids of the D-configuration and $X^3$ is an amino acid of the L-configuration and in which at least one of $X^2$-$X^3$-$X^4$ and $X^6$ is a randomized mixture of amino acids.

7. The combinatorial library of claim 6 wherein the amino acids are chosen from any of the α-amino acids.

8. A method of preparing a set of libraries of cyclic homodetic penta- or hexa-peptides containing a randomized mixture of amino acids at one or more positions, a defined and a constant amino acid in at least one position and wherein the peptide backbone of the library has a well-defined peptide backbone conformation, provided that the cyclic hexapeptide or pentapeptide contain a conformationally constraining element selected form Pro-D-Pro or D-pro-Gly-pro; which comprises:

a) coupling to a resin in any order:
   (1) an equimolar mixture of a randomized protected amino acid set in an amount equal to the number of reactive functional groups on the resin;
   (2) a constant protected amino acid; or
   (3) separating the resin into n separate aliquots and coupling a defined amino acid to each aliquot, wherein n is the number of protected amino acid residues in the defined amino acid set; or (b) removing the protective group from a reactive functional group on the amino acid;

(c) repeating step (a) and coupling the next residue to the reactive functional group of the previous amino acid until five or six residues have been added, (d) cleaving the peptide from the resin, (e) cyclizing the peptide, and (f) removing any protective groups, provided that the cyclic hexapeptide or pentapeptide contain the element Pro-D-Pro or D-pro-Gly-pro.

9. A method of preparing a set of libraries of cyclic homodetic pents-or hexa-peptides containing a randomized mixture of amino acids at one or more positions, a defined and constant amino acid in at least one position and wherein the peptide backbone of the library has a well-defined peptide backbone conformation, provided that the cyclic hexapeptide or pentapeptide contain a conformationally constraining element selected form Pro-D-Pro or D-pro-Gly-pro; which comprises:

a) dividing a resin into n different aliquots, wherein n is the number of amino acid residues in the defined amino acid set;

b) coupling exhaustively to each aliquot in any order:
  (1) a single equimolar random amino acid of the set;
  (2) a constant amino acid; or
  (3) a defined amino acid;

c) recombining and mixing the aliquots containing the random amino acids;

d) removing the protective group from a reactive functional group on the amino acid;

e) repeating steps (a) to (d) to couple the next residue if the next residue is a random or defined amino acid, or repeating steps (b) to (d) to couple the next residue if the next residue is a constant amino acid, until five or six residues have been added, f) cleaving the peptide from the resin, g) cyclizing the peptide, and h) removing any protective groups, provided that the cyclic hexapeptide or pentapeptide contain the element Pro-D-Pro or D-pro-Gly-pro.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 6 amino acids
      (B) TYPE: amino acid
      (D) TOPOLOGY: linear (ii) MOLECULE TYPE: peptide (ix) FEATURE:
      (A) NAME/KEY: Modified-site
      (B) LOCATION: 1..2
      (D) OTHER INFORMATION: /note= "known/defined amino acid"

```
        (xi) SEQUENCE DESCRIPTION: SEQ ID NO: 1:

Xaa Xaa Xaa Xaa Xaa Xaa
1               5

(2) INFORMATION FOR SEQ ID NO: 2:

(i) SEQUENCE CHARACTERISTICS:
         (A) LENGTH: 6 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1..4
         (D) OTHER INFORMATION: /note= "known/defined amino acids"

(xi) SEQUENCE DESCRIPTION: SEQ ID NO: 2:

Xaa Xaa Xaa Xaa Xaa Xaa
1               5

(2) INFORMATION FOR SEQ ID NO: 3:

(i) SEQUENCE CHARACTERISTICS:
         (A) LENGTH: 6 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "known/defined amino acid"

(xi) SEQUENCE DESCRIPTION: SEQ ID NO: 3:

Xaa Xaa Xaa Xaa Xaa Xaa
1               5

(2) INFORMATION FOR SEQ ID NO: 4:

(i) SEQUENCE CHARACTERISTICS:
         (A) LENGTH: 6 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /note= "known/defined amino acid"

(xi) SEQUENCE DESCRIPTION: SEQ ID NO: 4:

Xaa Xaa Xaa Xaa Xaa Xaa
1               5

(2) INFORMATION FOR SEQ ID NO: 5:

(i) SEQUENCE CHARACTERISTICS:
         (A) LENGTH: 6 amino acids
         (B) TYPE: amino acid
         (D) TOPOLOGY: circular (ii) MOLECULE TYPE: peptide (xi) SEQUENCE DESCRIPTION: SEQ ID NO: 5:

Xaa Xaa Xaa Xaa Xaa Xaa
```

```
1               5

(2) INFORMATION FOR SEQ ID NO: 6:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "known/defined amino acid"

(xi) SEQUENCE DESCRIPTION: SEQ ID NO: 6:

Xaa Xaa Xaa Xaa Xaa Xaa
1               5

(2) INFORMATION FOR SEQ ID NO: 7:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "known/defined amino acid"

(ix) FEATURE:
        (A) NAME/KEY: Modified-site
        (B) LOCATION: 3
        (D) OTHER INFORMATION: /note= "known/defined amino acid"

(xi) SEQUENCE DESCRIPTION: SEQ ID NO: 7:

Xaa Xaa Xaa Xaa Xaa Xaa
1               5

(2) INFORMATION FOR SEQ ID NO: 8:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "known/defined amino acid"

(ix) FEATURE:
        (A) NAME/KEY: Modified-site
        (B) LOCATION: 3
        (D) OTHER INFORMATION: /note= "known/defined amino acid"

(xi) SEQUENCE DESCRIPTION: SEQ ID NO: 8:

Xaa Xaa Xaa Xaa Xaa Xaa
1               5

(2) INFORMATION FOR SEQ ID NO: 9:

(i) SEQUENCE CHARACTERISTICS:
        (A) LENGTH: 6 amino acids
        (B) TYPE: amino acid
        (D) TOPOLOGY: circular
```

(ii) MOLECULE TYPE: peptide (ix) FEATURE:
        (A) NAME/KEY: Modified-site
        (B) LOCATION: 1..2
        (D) OTHER INFORMATION: /note= "known/defined amino acids"

(xi) SEQUENCE DESCRIPTION: SEQ ID NO: 9:

Xaa Xaa Xaa Xaa Xaa Xaa
1               5

(2) INFORMATION FOR SEQ ID NO: 10:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1..4
        (D) OTHER INFORMATION: /note= "known/defined amino acids"

(xi) SEQUENCE DESCRIPTION: SEQ ID NO: 10:

Xaa Xaa Xaa Xaa Xaa Xaa
1               5

(2) INFORMATION FOR SEQ ID NO: 11:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1..3
        (D) OTHER INFORMATION: /note= "known/defined amino acids"

(ix) FEATURE:
        (A) NAME/KEY: Peptide
        (B) LOCATION: 5
        (D) OTHER INFORMATION: /note= "known/defined amino acid"

(xi) SEQUENCE DESCRIPTION: SEQ ID NO: 11:

Xaa Xaa Xaa Xaa Xaa Xaa
1               5

(2) INFORMATION FOR SEQ ID NO: 12:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1..5
        (D) OTHER INFORMATION: /note= "known/defined amino acids"

(xi) SEQUENCE DESCRIPTION: SEQ ID NO: 12:

Xaa Xaa Xaa Xaa Xaa Xaa
1               5

(2) INFORMATION FOR SEQ ID NO: 13:

(i) SEQUENCE CHARACTERISTICS:
       (A) LENGTH: 6 amino acids
       (B) TYPE: amino acid
       (D) TOPOLOGY: circular (ii) MOLECULE TYPE: peptide (ix) FEATURE:
       (A) NAME/KEY: Modified-site
       (B) LOCATION: 1
       (D) OTHER INFORMATION: /note= "known/defined amino acid"

(ix) FEATURE:
       (A) NAME/KEY: Modified-site
       (B) LOCATION: 4
       (D) OTHER INFORMATION: /note= "known/defined amino acid"

(xi) SEQUENCE DESCRIPTION: SEQ ID NO: 13:

Xaa Xaa Xaa Xaa Xaa Xaa
1               5

(2) INFORMATION FOR SEQ ID NO: 14:

(i) SEQUENCE CHARACTERISTICS:
       (A) LENGTH: 6 amino acids
       (B) TYPE: amino acid
       (D) TOPOLOGY: circular (ii) MOLECULE TYPE: peptide (ix) FEATURE:
       (A) NAME/KEY: Modified-site
       (B) LOCATION: 1
       (D) OTHER INFORMATION: /note= "known/defined amino acid"

(ix) FEATURE:
       (A) NAME/KEY: Modified-site
       (B) LOCATION: 3..4
       (D) OTHER INFORMATION: /note= "known/defined amino acids"

(xi) SEQUENCE DESCRIPTION: SEQ ID NO: 14:

Xaa Xaa Xaa Xaa Xaa Xaa
1               5

(2) INFORMATION FOR SEQ ID NO: 15:

(i) SEQUENCE CHARACTERISTICS:
       (A) LENGTH: 6 amino acids
       (B) TYPE: amino acid
       (D) TOPOLOGY: circular (ii) MOLECULE TYPE: peptide (ix) FEATURE:
       (A) NAME/KEY: Modified-site
       (B) LOCATION: 1
       (D) OTHER INFORMATION: /note= "known/defined amino acid"

(ix) FEATURE:
       (A) NAME/KEY: Modified-site
       (B) LOCATION: 4..5
       (D) OTHER INFORMATION: /note= "known/defined amino acids"

(xi) SEQUENCE DESCRIPTION: SEQ ID NO: 15:

Xaa Xaa Xaa Xaa Xaa Xaa
1               5

(2) INFORMATION FOR SEQ ID NO: 16:

(i) SEQUENCE CHARACTERISTICS:
       (A) LENGTH: 6 amino acids

-continued

```
        (B) TYPE: amino acid
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "known/defined amino acid"

(ix) FEATURE:
        (A) NAME/KEY: Modified-site
        (B) LOCATION: 3
        (D) OTHER INFORMATION: /note= "known/defined amino acid"

(ix) FEATURE:
        (A) NAME/KEY: Modified-site
        (B) LOCATION: 5
        (D) OTHER INFORMATION: /note= "known/defined amino acid"

(xi) SEQUENCE DESCRIPTION: SEQ ID NO: 16:

Xaa Xaa Xaa Xaa Xaa Xaa
1               5
```